United States Patent
Roberts

(10) Patent No.: US 10,639,190 B2
(45) Date of Patent: May 5, 2020

(54) TEMPERATURE-REGULATING SPORTS WRAP WITH ANGLED ATTACHMENTS

(71) Applicant: MONTEREY BAY ASSOCIATES, Aptos, CA (US)

(72) Inventor: Dave Roberts, Aptos, CA (US)

(73) Assignee: MONTEREY BAY ASSOCIATES, Aptos, CA (US)

( * ) Notice: Subject to any disclaimer, the term of this patent is extended or adjusted under 35 U.S.C. 154(b) by 213 days.

(21) Appl. No.: 15/450,737

(22) Filed: Mar. 6, 2017

(65) Prior Publication Data

US 2017/0258631 A1    Sep. 14, 2017

Related U.S. Application Data

(60) Provisional application No. 62/305,089, filed on Mar. 8, 2016.

(51) Int. Cl.
*A61F 7/02* (2006.01)
*A61F 7/00* (2006.01)

(52) U.S. Cl.
CPC ........ *A61F 7/02* (2013.01); *A61F 2007/0042* (2013.01); *A61F 2007/023* (2013.01); *A61F 2007/0231* (2013.01)

(58) Field of Classification Search
CPC ........ A61F 2007/0228; A61F 2007/023; A61F 2007/0231; A61F 2007/0225; A61F 7/02; A61F 7/10; A61F 5/0104; A61F 5/0106; A61F 5/0118; A61F 5/02; A61F 5/03; A41C 1/02; A41C 1/08; A41C 1/10; A41D 2300/30; A41D 2300/32; A41D 2300/324; A41D 2300/326

See application file for complete search history.

(56) References Cited

U.S. PATENT DOCUMENTS

| | | | | |
|---|---|---|---|---|
| 5,314,455 A | * | 5/1994 | Johnson, Jr. | A61F 7/08 607/104 |
| 5,697,962 A | * | 12/1997 | Brink | A61F 7/02 126/204 |
| 6,545,193 B1 | * | 4/2003 | Morgenstern | A61F 13/0273 128/876 |
| 6,585,673 B1 | * | 7/2003 | Bass | A61F 7/02 128/845 |
| 6,656,210 B1 | * | 12/2003 | Plewes | A61F 7/02 128/DIG. 15 |

* cited by examiner

*Primary Examiner* — Joseph A Stoklosa
*Assistant Examiner* — Adam J Avigan
(74) *Attorney, Agent, or Firm* — Greer, Burns & Crain Ltd.

(57) ABSTRACT

A temperature-regulating sports wrap is provided, including a first web of fabric having elongate side edges and first and second end edges, a second web of fabric is secured to the first web of fabric. At least one pocket is defined between opposing surfaces of the first and second webs and opens along one of the elongate side edges. At least one first strip extends outwardly from the first side edges along an axis parallel to the elongate side edges, has one of a hook-and-loop fastener material. At least one second strip extends inwardly from the second side edges, is secured to a surface of one of the first and second webs. The at least one second strip has the opposite one of a hook-and-loop fastener material from the at least one first strip, the at least one second strip extends inwardly at a non-parallel angle from the second edge.

14 Claims, 5 Drawing Sheets

TEMPERATURE-REGULATING SPORTS WRAP WITH ANGLED ATTACHMENTS

RELATED APPLICATION

The present application claims 35 USC 119 priority from U.S. Provisional Application Ser. No. 62/305,089 filed Mar. 8, 2016.

BACKGROUND

The present invention relates generally to sports wraps used for treating sore muscles, joints or limbs strained or injured through exercise or injury, including but not limited to shoulders, elbows, knees, ankles, wrists and the like, and more specifically to an improved temperature-regulating sports wrap with improved attachments.

Conventional sports wraps include an elongate, polymeric foam device defining a pocket dimensioned for receiving a temperature-regulating element, such as a gel pack, hot pack, cold pack or other known temperature-generating element, including such elements configured to expand and/or generate desired temperatures upon application of water or the like. The temperature-regulating element, once inserted in the pocket, emits cold or hot temperature to the afflicted body part as desired. Conventional wraps include regions of VELCRO® hook-and-loop fastener material or the like for securing ends of the wrap device in a designated part of the body. Often the material used for the wrap device is incorporated with elastic or other stretchable material to enhance the fit of the device to the user.

However, due to the irregular shape of user's limbs and joints, conventional sports wraps are often difficult to secure adequately to the afflicted area for proper delivery of the desired hot/cold temperature of the temperature-regulating element. Even if initially tight, the wraps soon loosen. Alternately, the conventional wraps often slacken to the extent that the temperature-regulating element is no longer held against the designated afflicted area, so that the effectiveness of the element is lost, and the soreness or other affliction is not ameliorated.

Thus, there is a need for an improved sports wrap that addresses the above-listed drawbacks.

SUMMARY

The above-listed need is met or exceeded by the present temperature-regulating sports wrap, which features a pair of webs of material joined together to form at least one pocket dimensioned for retaining at least one temperature-regulating element. One end edge of the wrap has a pair of strips extending from the edge, and each of the strips extends parallel with elongate edges of the wrap and has one of a hook-and-loop fastener material. An opposite end edge of the wrap has a pair of strips extending inwardly from the corresponding end edge and secured to the wrap to form a non-linear angle relative to the first strips.

A feature of the present wrap is that, upon engagement of each first strip with the corresponding second strip, the hook-and-loop fastener materials are engaged with each other along a non-linear axis so that transverse forces are exerted by each first strip relative to each second strip. Such engagement has been found to be more positive than conventional wraps with linearly aligned straps or strips, and maintains the wrap more securely in a designated location on the body.

More specifically, a temperature-regulating sports wrap is provided, including a first web of fabric having elongate side edges and relatively shorter first and second end edges, a second web of fabric secured to the first web of fabric. The second web also has elongate side edges and first and second end edges in registry with said edges of the first web. At least one pocket is defined in a space created between opposing surfaces of the first and second webs and is constructed and arranged to open along one of the elongate side edges. At least one first strip extends outwardly from the first side edges along an axis parallel to the elongate side edges, has one of a hook-and-loop fastener material. At least one second strip extends inwardly from the second side edges, is secured along its length to an outer surface of one of the first and second webs. The at least one second strip has the opposite one of a hook-and-loop fastener material from the at least one first strip, the at least one second strip extends inwardly at a non-parallel angle from the second edge.

In another embodiment, a temperature-regulating sports wrap is provided including a first web of fabric having elongate first side edges and relatively shorter first and second end edges, a second web of fabric is secured to the first web of fabric and has elongate second side edges and first and second end edges in registry with the edges of the first web. At least one pocket is defined in a space created between opposing surfaces of the first and second web and is constructed and arranged to open along one of the elongate side edges. A pair of first strips extends outwardly from the first side edges along an axis parallel to the elongate first and second side edges and each has the same one of a hook-and-loop fastener material. A pair of second strips extends inwardly from the second side edges, secured along a length of each strip to an outer surface of one of first and second webs. Each second strip has the opposite one of a hook-and-loop fastener material from the pair of first strips, each second strip extending inwardly at a non-parallel angle from the second edge such that upon the first strips each respectively engaging one of the second strips, the corresponding one of hook-and-loop material on the first strips engage the corresponding hook-and-loop material on the second strip so as to create an attachment force transverse or nonlinear to an axis of the second strip.

DETAILED DESCRIPTION

Figure 1:
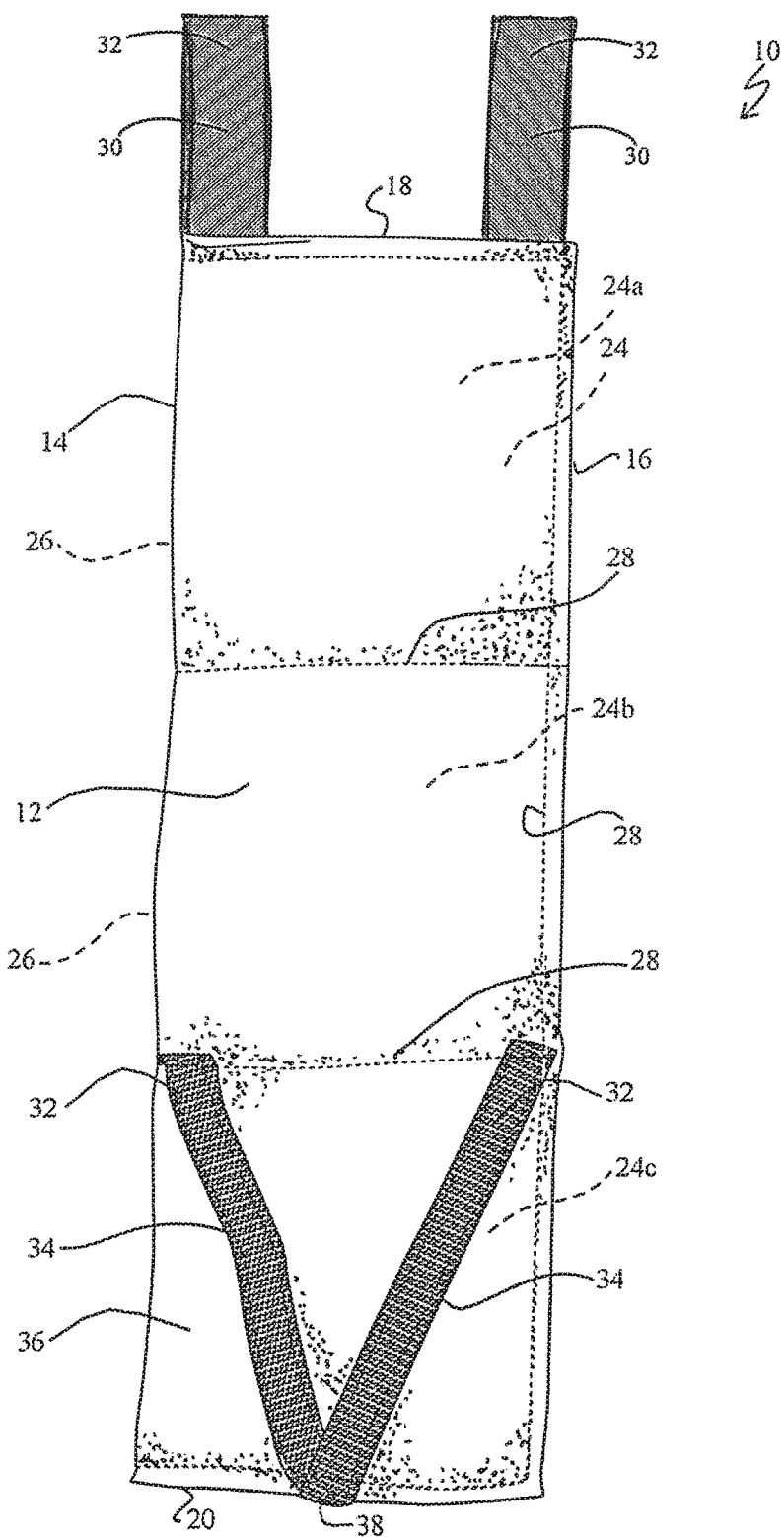
FIG. 1 is a top view of a first embodiment of the present sports wrap.

Referring now to FIGS. 1-5, the present sports wrap is generally designated 10, and includes a first web or sheet of fabric 12 having elongate side edges 14, 16 and relatively shorter first and second end edges 18, 20. The web 12 is made of any suitable, durable and washable material, but flexible Neoprene® closed-cell foam fabric or the like is preferred. A second web or sheet of fabric 22 (FIG. 3) is secured to the first web of fabric 12 by stitching, chemical adhesive, ultrasonic welding or the like and also has elongate side edges 14, 16 and first and second end edges 18, 20 in registry with the edges of the first web.

At least one pocket 24 is defined in a space 26 created between opposing surfaces of the first and second webs 12, 22 and is constructed and arranged to open along one of the elongate side edges 14, 16. The preferably three pockets 24a, 24b, 24c are defined in the space 26 by fastening 28, preferably stitching or other suitable fastening techniques, including adhesive, rivets and ultrasonic welding.

At least one first strip 30 extends outwardly or away from the first end edges 18 along an axis parallel to the elongate side edges 14, 16 and has one of a hook-and-loop fastener material 32, preferably VELCRO® hook-and-loop material. There is preferably a pair of first strips 30 spaced along the edges 18, and the strips are preferably elastic nylon or equivalent stretchable, sturdy fabric material. In the preferred embodiment, the first strips 30 extend from an approximate length of 3 inches to approximately 5-6 inches when stretched.

At least one second strip 34 extends inwardly from the second end edges 20 and is secured along its length to an outer surface 36 of one of the first and second webs 12, 22, and having the opposite one of the hook-and-loop fastener material 32 from each first strip 30. The at least one and preferably two second strips 34 extend inwardly, or towards the opposite end edge 18 at a non-parallel angle from the second edge 20.

Figure 3:
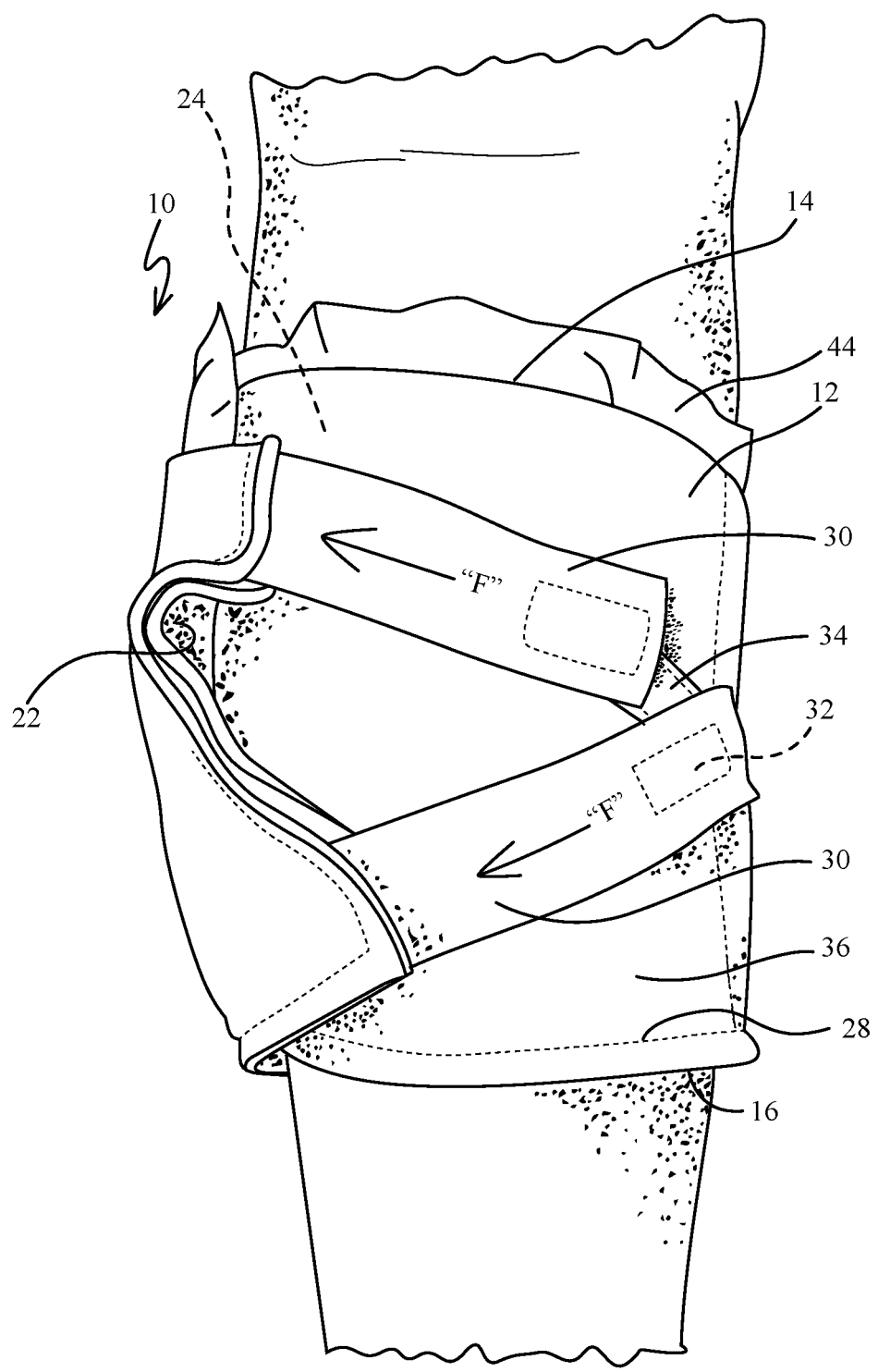
FIG. 3 is a front view of the embodiment of FIG. 1 wrapped around a knee.
Figure 4:
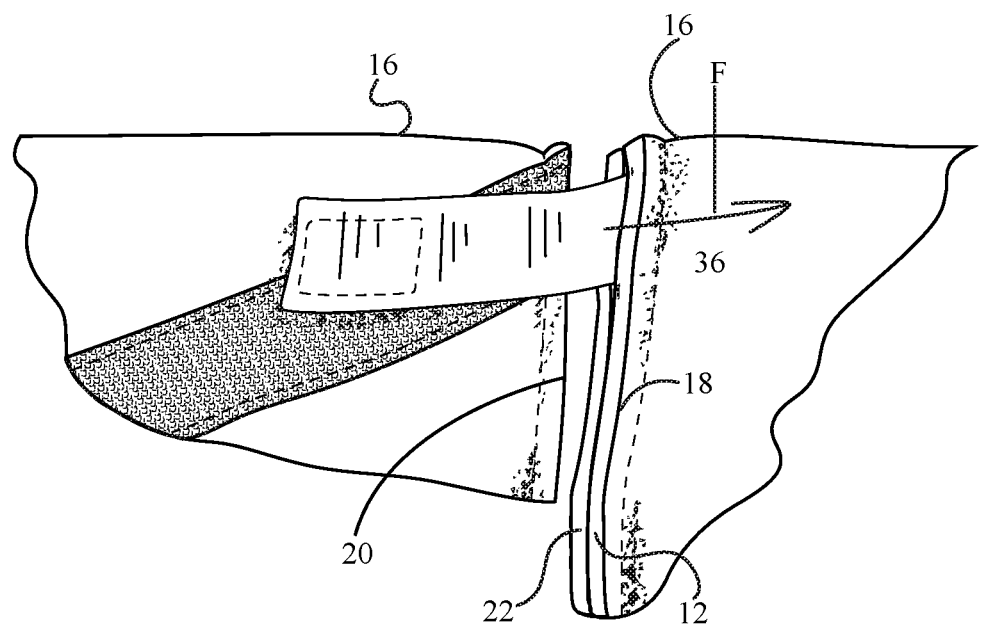
FIG. 4 is an enlarged fragmentary top view of the engagement of the first and second strips of the present wrap.

Referring now to FIGS. 3 and 4, a feature of the present sports wrap 10 arises out of the non-parallel orientation of the second strips 34 relative to the first strips 30. Upon fastening engagement of the complementary hook-and-loop fastener materials 32 of an associated pair of the first and second strips 30, 34, the hook-and-loop fastener materials are engaged with each other along a non-linear axis so that transverse or forces "F" misaligned with the second strips 34 are exerted by the first strip 30 relative to the corresponding second strip 34. In other words, the hook-and-loop material 32 on the first strips 30 pulls on the material of the corresponding second strip 34 transversely or nonlinearly to a linear axis of the second strip.

Another factor in the engagement is that the second strips 34 are fixed to the web 12, 22, and the first strips 30 are elastically pulled into position upon the second strips. This engagement has been found to result in a more secure engagement of the strips 30, 34 compared to conventional sports wraps, and as such, the present sports wrap 10 is more securely held around the target limb or area for applying the desired temperature therapy (FIG. 3).

Figure 5:
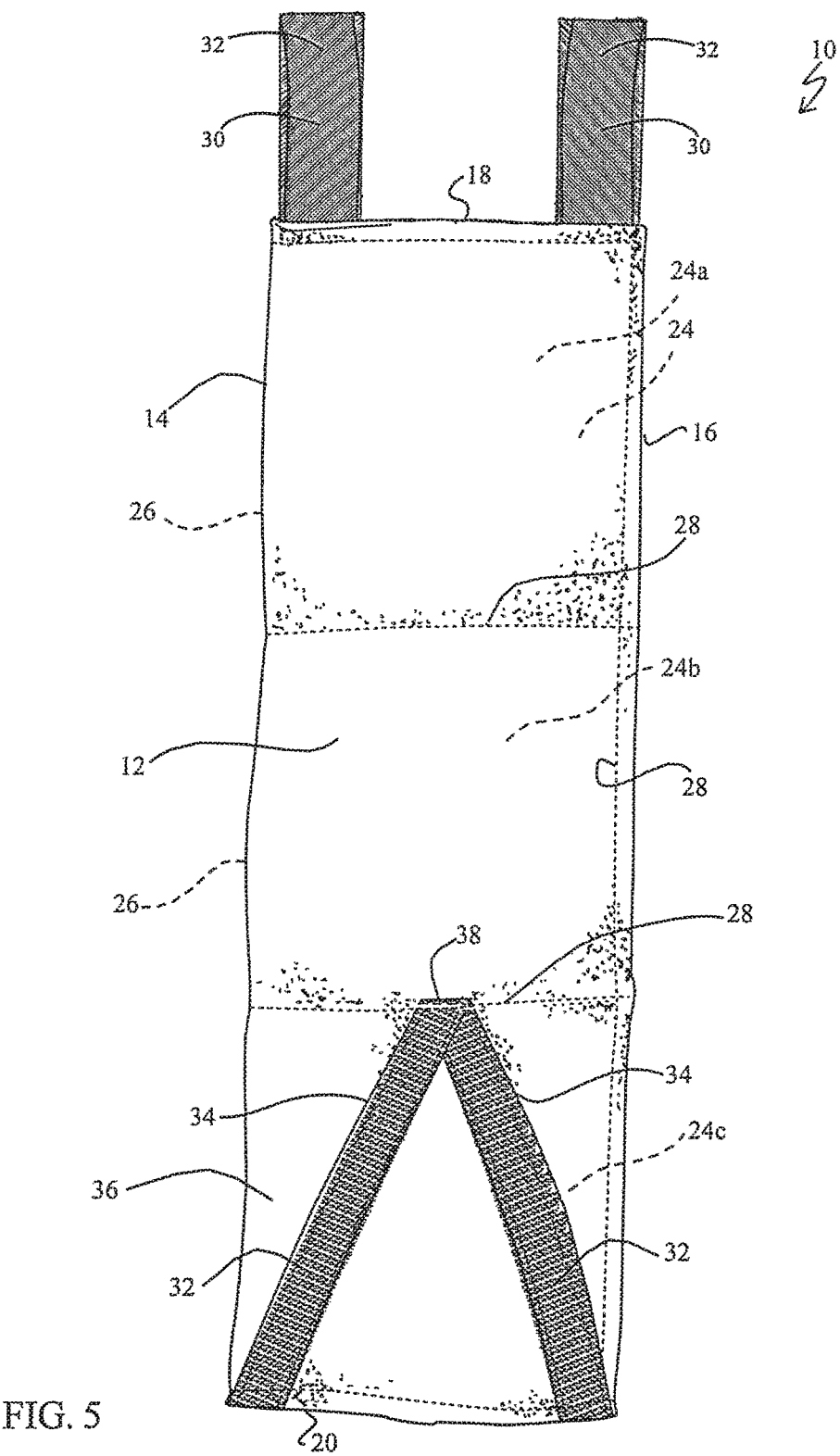
FIG. 5 is a top view of a third embodiment of the present sports wrap.

As seen in FIG. 1, the second strips 34 are preferably provided as a pair of such strips oriented in a general "V"-shape on the outer surface 36 of the web 12, 22. In this embodiment, a point 38 of the "V"-shape is directed towards the corresponding end edge 20. It is also contemplated that the point 38 is alternately directed to the other end edge 18 (FIG. 5).

Figure 2:
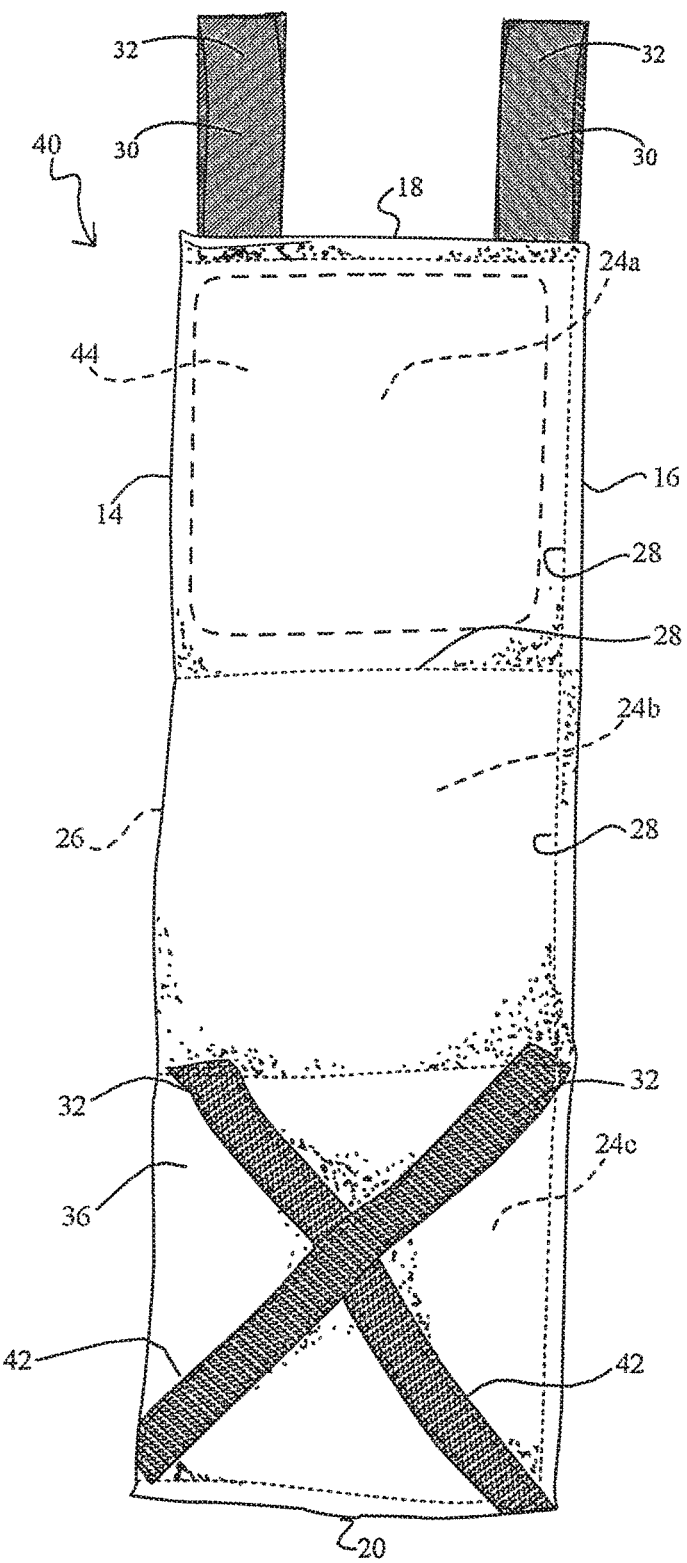
FIG. 2 is a top view of a second embodiment of the present sports wrap.

Referring now to FIG. 2, an alternate embodiment of the sports wrap 10 is shown and generally designated 40. Components shared with the wrap 10 are designated with identical reference numbers. A main difference between the wrap 40 and the wrap 10 is that in the former, instead of being oriented in a "V"-shape, the at least one second strip 42 includes a pair of such strips oriented in a general "X"-shape on the outer surface 36 of the web 12, 22. The sports wrap 40 also features the property that the first strips 30 engage the second strips 42 so that the forces "F" are generated transverse or non-linear when the complementary hook-and-loop materials 32 engage each other.

It will be seen in FIGS. 1 and 2 that the at least one second strip 34, 42 is disposed on the outer web surface 36 adjacent the pocket 24c closest to the corresponding end edge 18, 20. Also, a heating or cooling element 44, such as a gel pack or other known temperature-regulating pack is insertable into the pockets 24a-c.

While a particular embodiment of the present temperature-regulating sports wrap with angled attachments has been described herein, it will be appreciated by those skilled in the art that changes and modifications may be made thereto without departing from the invention in its broader aspects and as set forth in the following claims.

The invention claimed is:

1. A sports wrap, comprising:
   a first web of fabric having elongate side edges and relatively shorter first and second end edges;
   a second web of fabric secured to said first web of fabric and having elongate side edges and first and second end edges in registry with said edges of said first web;
   at least one pocket defined in a space created between opposing surfaces of said first and second webs and constructed and arranged to open along one of said elongate side edges;
   at least one first strip extending outwardly from said first end edges along an axis parallel to said elongate side edges and having one of a hook material or loop material of a hook-and-loop fastener; and
   at least one second strip extending inwardly from said second end edges, being secured along its length to an outer surface of one of said first and second webs, and having the opposite one of a hook material or loop material of a hook-and-loop fastener from said at least one first strip, said at least one second strip extending inwardly at a non-perpendicular angle relative to said second end edge which is also non-parallel to said elongate side edges;
   wherein said at least one second strip includes a pair of such strips oriented in a general "V"-shape on said outer surface of one of said first and second webs.

2. The sports wrap of claim 1 wherein a point of said "V"-shape is directed towards said corresponding one of said first or second end edges.

3. The sports wrap of claim 1, wherein three pockets are defined between said first and second webs, and said at least one second strip is disposed on said outer web surface adjacent the one of said pockets closest to said corresponding second end edge.

4. The sports wrap of claim 1, wherein each said at least one first strip is made of elastic material.

5. The sports wrap of claim 1, wherein said hook-and-loop fastener material of said at least one first strip is configured engaged with the hook-and-loop material of said at least one second strip along a non-linear axis and to exert transverse or nonlinear forces to said corresponding at least one second strip.

6. The sports wrap of claim 1, wherein said at least one first strip is elastic, and said one of hook-and-loop material on said at least one first strip is configured for engaging the complementary one of hook-and-loop material on said at least one second strip such that said elastic first strip pulls said hook-and-bop material transversely to a linear axis of said at least one second strip.

7. A sports wrap, comprising:
   a first web of fabric having elongate side edges and relatively shorter first and second end edges;

a second web of fabric secured to said first web of fabric and having elongate side edges and first and second end edges in registry with said edges of said first web;

at least one first strip extending outwardly from said first end edges along an axis parallel to said elongate side edges and having one of a hook material or loop material of a hook-and-loop-fastener; and at least one second strip extending inwardly from said second end edges, being secured along its length to an outer surface of one of said first and second webs, and having the opposite one of a hook material or loop material of a hook-and-loop fastener from said at least one first strip, said at least one second strip extending inwardly at a non-perpendicular angle relative to said second end edge which is also non-parallel to said elongate side edges, wherein said at least one second strip includes a pair of such strips oriented in a general "X"-shape on said outer surface of one of said first and second webs.

8. The sports wrap of claim 7, wherein three pockets are defined between said first and second webs, and said at least one second strip is disposed on said outer web surface adjacent the one of said pockets closest to said corresponding second end edge.

9. The sports wrap of claim 7, wherein each said at least one first strip is made of elastic material.

10. The sports wrap of claim 7, wherein said hook-and-loop fastener material of said at least one first strip is configured to be engaged with the hook-and-loop material of said at least one second strip along a non-linear axis and to exert transverse or nonlinear forces to said corresponding at least one second strip.

11. The sports wrap of claim 7, wherein said at least one first strip is elastic, and said one of hook-and-loop material on said at least one first strip is configured for engaging the complementary one of hook-and-loop material on said at least one second strip such that said elastic first strip pulls said hook-and-loop material transversely to a linear axis of said at least one second strip.

12. A sports wrap, comprising:
a first web of fabric having elongate side edges and relatively shorter first and second end edges;

a second web of fabric secured to said first web of fabric and having elongate side edges and first and second end edges in registry with said edges of said first web;

at least one pocket defined in a space created between opposing surfaces of said first and second webs and constructed and arranged to open along one of said elongate side edges;

at least one first strip extending outwardly from said first end edges along an axis parallel to said elongate side edges and having one of a hook material or loop material of a hook-and-loop fastener; and a pair of second strips extending inwardly relative to said second end edges, each said second strip being secured along its length to an outer surface of one of said first and second webs, and having the opposite one of a hook material or loop material of a hook-and-loop fastener from said at least one first strip, said at least one second strip extending inwardly at a non-perpendicular angle from said second end edge which is also non-parallel to said elongate side edges, and each said second strips having a length and overlapping each other along a portion of said length.

13. The sports wrap of claim 12 wherein each said second strip has one end secured to said web adjacent a corresponding elongate side edge, and an opposite end secured to said second end edge.

14. The sports wrap of claim 12 wherein each said second strip has one end secured to said web adjacent a first corresponding elongate side edge, and an opposite end secured adjacent to a second elongate side edge opposite said first elongate side edge.

* * * * *